(12) United States Patent
De Haan et al.

(10) Patent No.: US 11,810,325 B2
(45) Date of Patent: Nov. 7, 2023

(54) METHOD, DEVICE AND SYSTEM FOR ENABLING TO ANALYZE A PROPERTY OF A VITAL SIGN DETECTOR

(71) Applicant: KONINKLIJKE PHILIPS N.V., Eindhoven (NL)

(72) Inventors: Gerard De Haan, Helmond (NL); Ihor Olehovych Kirenko, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 116 days.

(21) Appl. No.: 16/090,838

(22) PCT Filed: Apr. 6, 2017

(86) PCT No.: PCT/EP2017/058277
§ 371 (c)(1),
(2) Date: Oct. 3, 2018

(87) PCT Pub. No.: WO2017/174735
PCT Pub. Date: Oct. 12, 2017

(65) Prior Publication Data
US 2019/0108650 A1    Apr. 11, 2019

(30) Foreign Application Priority Data
Apr. 6, 2016   (EP) .................................... 16163994

(51) Int. Cl.
*G06T 7/80*     (2017.01)
*A61B 5/00*     (2006.01)
(Continued)

(52) U.S. Cl.
CPC .............. *G06T 7/80* (2017.01); *A61B 5/0077* (2013.01); *A61B 5/0205* (2013.01); *A61B 5/744* (2013.01);
(Continued)

(58) Field of Classification Search
CPC .............. A61B 2090/365; A61B 34/10; A61B 2034/107; A61B 2090/376;
(Continued)

(56) References Cited

U.S. PATENT DOCUMENTS

| 4,408,124 A | 10/1983 | Paras |
| 6,847,336 B1 * | 1/2005 | Lemelson .............. H04N 7/147 345/8 |

(Continued)

FOREIGN PATENT DOCUMENTS

| EP | 3096254 A1 * | 11/2016 | ........... A61B 5/0006 |
| WO | 2015027286 A1 | 3/2015 | |

OTHER PUBLICATIONS

Wieringa et al. "Contactless Multiple Wavelength Photoplethysmo—Graphic Imaging: A First Step Toward "SpO2 Camera" Technology", Annals of Biomedical Engineering, vol. 33, No. 8, Aug. 2005.
(Continued)

*Primary Examiner* — Daniel Chang (57) ABSTRACT

The present invention relates to a method and a device for enabling to analyze a property of a vital sign detector (20). The proposed method comprises the steps of providing a virtual phantom (14) of a living being, rendering an artificial vital sign on the displayed virtual phantom (14), and outputting the virtual phantom (14) with the rendered artificial vital sign to the vital sign detector (20).

20 Claims, 2 Drawing Sheets

(51) Int. Cl.
  *G09B 23/28* (2006.01)
  *A61B 5/0205* (2006.01)
  *A61B 5/021* (2006.01)
  *A61B 5/024* (2006.01)
  *A61B 5/08* (2006.01)
  *A61B 5/11* (2006.01)
  *A61B 5/1455* (2006.01)

(52) U.S. Cl.
  CPC .............. *G09B 23/28* (2013.01); *A61B 5/021* (2013.01); *A61B 5/02433* (2013.01); *A61B 5/0816* (2013.01); *A61B 5/1128* (2013.01); *A61B 5/1455* (2013.01); *A61B 2560/0223* (2013.01); *A61B 2560/0233* (2013.01); *G06T 2207/10024* (2013.01); *G06T 2207/10048* (2013.01); *G06T 2207/10152* (2013.01)

(58) Field of Classification Search
  CPC ...... A61B 2090/3762; A61B 2090/373; A61B 17/1703; A61B 90/36; A61B 5/742; A61B 5/0077; A61B 2576/00; A61B 2034/2065; A61B 5/0013; G06T 7/0012; G06T 2207/30196; G06T 15/205; G06T 2207/10052; G06T 2210/41
  See application file for complete search history.

(56) References Cited

U.S. PATENT DOCUMENTS

| | | | |
|---|---|---|---|
| 7,748,252 B2 | 7/2010 | Bakker | |
| 8,704,895 B2 | 4/2014 | Safaee-Rad | |
| 8,773,540 B2 | 7/2014 | Friend | |
| 8,811,692 B2 | 8/2014 | Prokoski | |
| 10,201,281 B2 | 2/2019 | Adams | |
| 10,729,502 B1* | 8/2020 | Wolf | G06Q 10/063112 |
| 11,553,969 B1* | 1/2023 | Lang | G06T 7/0012 |
| 2002/0190972 A1* | 12/2002 | Ven de Van | G09F 9/30 345/204 |
| 2005/0001991 A1* | 1/2005 | Ulichney | H04N 5/74 353/69 |
| 2005/0099501 A1* | 5/2005 | Kang | G06T 5/006 348/207.99 |
| 2005/0231596 A1* | 10/2005 | Marchese | H04N 17/002 348/187 |
| 2005/0249399 A1* | 11/2005 | Tek | G06T 7/11 382/154 |
| 2007/0076101 A1* | 4/2007 | Baer | H04N 17/002 348/222.1 |
| 2008/0062164 A1* | 3/2008 | Bassi | H04N 9/3194 345/214 |
| 2008/0221399 A1* | 9/2008 | Zhou | G16H 40/67 600/301 |
| 2008/0293025 A1* | 11/2008 | Zamierowsi | G09B 23/28 434/262 |
| 2009/0112072 A1* | 4/2009 | Banet | A61B 5/7445 600/301 |
| 2010/0056897 A1* | 3/2010 | Zhang | A61B 6/541 600/407 |
| 2010/0130875 A1* | 5/2010 | Banet | A61B 5/02125 600/490 |
| 2010/0160798 A1* | 6/2010 | Banet | A61B 5/02133 600/490 |
| 2010/0179428 A1* | 7/2010 | Pedersen | A61B 8/4254 600/443 |
| 2010/0191541 A1* | 7/2010 | Prokoski | G16H 30/40 705/2 |
| 2010/0298650 A1* | 11/2010 | Moon | A61B 5/044 600/301 |
| 2011/0066007 A1* | 3/2011 | Banet | A61B 5/1116 600/301 |
| 2011/0066043 A1* | 3/2011 | Banet | A61B 5/022 600/485 |
| 2011/0085711 A1* | 4/2011 | Nagasaka | B60R 25/255 382/124 |
| 2012/0057674 A1* | 3/2012 | Zhang | A61B 6/06 378/62 |
| 2012/0287287 A1* | 11/2012 | Grossmann | H04N 17/002 348/181 |
| 2013/0300573 A1* | 11/2013 | Brown | A61B 5/0002 340/870.01 |
| 2014/0155759 A1* | 6/2014 | Kaestle | A61B 5/0002 340/870.01 |
| 2014/0249431 A1* | 9/2014 | Banet | A61B 5/0022 600/485 |
| 2014/0287395 A1* | 9/2014 | Silverglate | G09B 23/28 434/266 |
| 2014/0303454 A1* | 10/2014 | Clifton | G06T 5/008 600/301 |
| 2015/0105670 A1* | 4/2015 | Bresch | A61B 5/0077 600/479 |
| 2015/0149217 A1* | 5/2015 | Rath | G16H 40/63 705/3 |
| 2015/0327800 A1* | 11/2015 | Chen | H04N 5/2352 600/480 |
| 2015/0379901 A1* | 12/2015 | Welch | G09B 23/30 434/267 |
| 2016/0086500 A1* | 3/2016 | Kaleal, III | G06Q 10/10 434/257 |
| 2016/0314710 A1* | 10/2016 | Jarc | G09B 23/28 |
| 2017/0238805 A1* | 8/2017 | Addison | A61B 5/7278 |
| 2017/0239491 A1* | 8/2017 | Xia | A61B 5/004 |
| 2018/0103916 A1* | 4/2018 | Tscholl | A61B 5/744 |
| 2021/0192759 A1* | 6/2021 | Lang | G06T 3/40 |

OTHER PUBLICATIONS

Verkruysse et al., "Remote plethysmographic imaging using ambient light", Optics Express, 16(26), Dec. 22, 2008, pp. 21434-21445.

* cited by examiner

METHOD, DEVICE AND SYSTEM FOR ENABLING TO ANALYZE A PROPERTY OF A VITAL SIGN DETECTOR

CROSS REFERENCE TO RELATED APPLICATIONS

This application is the U.S. National Phase application under 35 U.S.C. §371 of International Application No. PCT/EP2017/058277, filed Apr. 6, 2017, published as WO 2017/174735 on Oct. 12, 2017, which claims the benefit of European Patent Application Number 16163994.3 filed Apr. 6, 2016. These applications are hereby incorporated by reference herein.

FIELD OF THE INVENTION

The present invention relates to a method, a device and a system for enabling to analyze a property of a vital sign detector. In particular, the present invention relates to calibrating or testing vital signs cameras for monitoring various vital signs such as pulse, oxygenation level, respiration, etc.

BACKGROUND OF THE INVENTION

Health monitoring is traditionally present in the hospital, particularly the ICU and includes the monitoring of vital signs like EEG, ECG, pulse-rate, respiratory rate, blood-oxygenation level, blood pressure, etc. Also sleep laboratories acquire information about sleeping subjects using actigraphy and electromyography, additionally to some of the other vital signs.

These application areas often involve multiple sensors attached to the body of the patient, some of which may be wireless and others wired, restricting the freedom to move or the quality of sleep of the patient, in addition to causing discomfort and possible skin-damage.

Video Health Monitoring is recently emerging as a promising unobtrusive alternative for an increasing number of the above health indicators, not the least driven by the strong wish to reduce the burden caused by current techniques to (pre-term) neonates and patients with extensive skin damage, e.g. due to burns.

Clearly, Video Health Monitoring, due to its unobtrusive character, adds to patient comfort even in cases where no real damage is done by the current technology. However, also new application fields emerge in the consumer domain, as simpler derived methods may run on consumer platforms like laptops, tablets and mobile phones, or on embedded platforms inside equipment used for exercise in the gym.

Video Health Monitoring is also emerging for use in analyzing the human skin, in particular with relevance for cosmetic industry (e.g. moisturizers advice) and dermatology (e.g. melanoma detection). Various diseases may be diagnosed from motion in video sequences, like Periodic Leg Movements, Delirium, while video analysis may reveal information about body posture with relevance in baby monitors to prevent Sudden Infant Death. Such motions that can be analyzed in order to extract the health condition of a patient are also understood as vital signs.

Consequently, there is a very broad application domain for Video Health Monitoring ranging from beauty product, the gym, consumer home-healthcare including baby-monitoring, sleep-center, the General Ward, the Intensive Care Unit, to the highly specialized Neonatal Intensive Care Unit and burn-center.

US 2015/0105670 A1 discloses a system for determining a vital sign of a subject, the system comprising an imaging unit for obtaining video data of the subject, a marker directly or indirectly attached to a body of the subject, wherein the marker comprises a graphical pattern, an image processing unit for detecting said marker in said video data, and an analysis unit adapted to extract a vital sign parameter related to the vital sign of the subject from said video data and to determine the vital sign from said vital sign parameter.

There is an increasing need to verify the calibration of these vital signs detectors, in particular cameras, once they are used widely in hospitals. Also, prior to admitting new detectors to the market, these detectors may need to be tested for the sake of adequate performance. Since the vital signs should be highly reliable to safely monitor the patient's health in high-risk (hospital) environments, correct calibration is crucial.

Wieringa et al. "CONTACTLESS MULTIPLE WAVELENGTH PHOTOPLETHYSMOGRAPHIC Imaging: A FIRST STEP TOWARD "$SpO_2$ Camera" Technology", Annals of Biomedical Engineering, Vol. 33, No. 8, August 2005, discloses a route toward contactless imaging of arterial oxygen saturation ($SpO_2$) distribution within tissue, based upon detection of a two-dimensional matrix of spatially resolved optical plethysmographic signals at different wavelength.

SUMMARY OF THE INVENTION

It is an object of the present invention to provide a method, a device and a system for enabling to analyze a property of a vital sign detector such that the vital signs can be detected with improved accuracy.

In a first aspect of the present invention a method for enabling to analyze a property of a vital sign detector is provided that comprises the steps of providing a virtual phantom of a living being, rendering one or more artificial vital signs on the virtual phantom, and outputting the virtual phantom with the rendered one or more artificial vital signs to the vital sign detector.

In a further aspect of the present invention, a device for enabling to analyze a property of a vital sign detector is provided that comprises a virtual phantom providing unit for providing a virtual phantom of a living being, a vital sign rendering unit for rendering one or more artificial vital signs on the virtual phantom, and an output unit for outputting the virtual phantom with the rendered one or more artificial vital signs to the vital sign detector.

In yet further aspects of the present invention, there are provided a computer program which comprises program code means for causing a computer to perform the steps of the method disclosed herein when the computer program is carried out on a computer as well as a non-transitory computer-readable recording medium that stores therein a computer program product, which, when executed by a device, causes the method disclosed herein to be performed.

Preferred embodiments of the invention are defined in the dependent claims. It shall be understood that the claimed device, computer program and computer-readable recording medium have similar and/or identical preferred embodiments as the claimed method, as defined in the dependent claims and as disclosed herein.

The present invention achieves an improved detection of vital signs with higher accuracy by enabling to more reliably analyze properties of the vital sign detector. The property may be related to a calibration procedure or a test procedure defined by the steps of the method claimed herein. Alternatively, the analyzed property may be evaluation of motion robustness or other properties of the vital sign detector. Further, the virtual phantom may be used to prove or at least determine the likelihood of a vital sign detector using a particular algorithm (e.g. for robust pulse-rate extraction, or $SpO_2$-computation).

A virtual phantom is a specially designed object that is scanned or imaged in the field of medical imaging to evaluate, analyze, and tune the performance of various imaging devices. The virtual phantom may contain the form of a face or a full body of a living being such as human, preferably a neonate. The phantom may be an image of a natural human face or body, or an image of a mannequin.

The virtual phantom may be generated by the device which carries out the claimed method, preferably a computer carrying out a corresponding software program. Alternatively, the virtual phantom may be generated by an external entity and subsequently transferred to the device to carry out the claimed method, e.g. via a communication interface or via wireless communication. The virtual phantom may be displayed on a display unit such as a RGB monitor.

The artificial vital signs may be associated with a pulse activity such as blood pressure, blood concentration (e.g. oxygen, glucose, bilirubin, CO, $CO_2$, . . . ), pulse rate (e.g. in the range 40-240 beats per minute (bpm)), oxygen saturation ($SpO_2$), and photoplethysmography (PPG) amplitude (e.g. a defined set of decreasing $SpO_2$ values starting at a saturation level of 100% down to 60%). The artificial vital signs may be alternatively associated with a respiratory activity such as respiratory rate (e.g. in the range 70-100 bpm) and vital capacity. In addition, the artificial vital signs may be associated with a motion such as one that is typical for chest breathing or abdominal breathing, or one that is typical for entering or leaving a bed, or one that is typical for various sleep stages such as body stretching or muscle contraction. The artificial vital signs may also be associated with a body temperature or any other physiological parameter.

The term "artificial" indicates that the vital signs do not actually originate from the virtual phantom itself. In particular, the artificial vital signs may be generated by using previously obtained results of vital sign measurements performed on a natural living being or natural tissues. Alternatively or additionally, the artificial vital signs may be, in contrast to natural vital signs of a natural living being or tissue, generated using computer simulation involving a mathematical model.

The artificial vital signs may be rendered using one or more phantom parameters for characterizing the provided virtual phantom. For instance, illumination of a human face or a scene background of the human face may be used as phantom parameters, so that a certain level of illumination and a certain scene background can be mimicked.

The artificial vital sign(s) may be rendered on the virtual phantom by means of a user interface, on which a parameter such as a numeral value or a text string, e.g. color, type of motion or activity level, may be selected.

The vital sign detector may be a vital sign camera, in particular a remote PPG camera or a sleep-actigraphy camera. It can also be a pulse oximeter or any other detector suitable for detecting a physiological parameter of a living being. Remote PPG is generally known in the art and described in many documents, e.g. in Verkruysse et al., "Remote plethysmographic imaging using ambient light", Optics Express, 16 (26), 22 Dec. 2008, pp. 21434-21445.

By outputting the virtual phantom, on which the artificial vital sign is rendered, to a vital sign detector, the present invention enables to analyze a property, e.g. to determine a setting related to calibration or testing of the vital sign detector. Virtual phantoms are made easily available and also configurable according to the actual need of the user. For instance, there can be a set of virtual phantoms each corresponding to a specific body part or a body part during a specific stage of an illness or treatment. Also, since the artificial vital sign is rendered independently from the vital sign detector, the reliability of the determination of the setting is increased. The present invention is particularly advantageous when a large number of vital sign detectors need to be calibrated or tested.

It is noted that providing a virtual phantom may mean creating or generating a new virtual phantom, or alternatively transferring or copying an existing virtual phantom. Further, it is also noted that outputting a virtual phantom may mean displaying a virtual phantom, or alternatively transferring a virtual phantom.

Preferably, at least one of the rendered artificial vital signs is temporally varying. For instance, when a value, e.g. amplitude, is assigned to the artificial vital sign, the artificial vital sign may vary temporally in its value. When the artificial vital sign refers to a motion of a living being that is to be identified by a vital sign detector, e.g. entering or leaving a bed, the artificial vital sign may vary temporally during various stages of the respective motion. In this way, dynamic vital signs can be rendered on the virtual phantom, so that the calibration or testing of the vital sign detector can take a variety of health conditions/states of a living being, in particular a patient or neonate, into account. This advantageously increases the reliability of the calibrated or tested vital sign detector. The rendered artificial vital sign may also be assigned a selection of parameters such as color, type of motion or activity level. Preferably, a static signal for a first artificial vital sign (e.g. $SpO_2$) may be rendered based on a time-varying signal for a second artificial vital sign (e.g. the pulse).

In particular, the rendered artificial vital sign may comprise a periodic variation of a shape, a volume, a position, an orientation and/or a color of the provided virtual phantom. Since a plurality of vital signs including pulse signals, respiratory signals and $SpO_2$ signals show periodic behaviors, the present invention enables to mimic natural human body parts or tissues with high accuracy using the virtual phantom. The color of the provided virtual phantom may be a pseudo-color which indicates the case where the "color" variations are rendered in the near-infrared (NIR) spectral range, so that the variations are not visible in contrast to color variations in the visible spectral range.

For instance, for the case that the virtual phantom contains the form of a human face, the artificial vital sign may comprise the skin color that varies periodically, thereby mimicking a periodic change in skin color of a natural human face due to the varying blood volume in the skin during the cardiac cycles or due to respiration. In this case, the artificial vital sign may be the pulse or pulse-rate or respiratory rate that can be output to the vital sign detector.

Alternatively, the rendered artificial vital sign may comprise a non-periodic variation of a shape, a volume, a position, an orientation and/or a color of the provided virtual phantom. For instance, the virtual phantom may contain a whole human body, wherein the artificial vital sign may comprise the body orientation that varies in a non-periodic manner, thereby mimicking a change in the body orientation of a person during sleep or when entering or leaving the bed. In this case, the artificial vital sign may be the (average)

frequency of turning the body during sleep, or a discrimination between the various sleep stages (shallow/deep sleep, REM-sleep, etc.).

Preferably, the step of providing and/or rendering comprises projecting, emitting and/or absorbing a plurality of images of the living being each for a corresponding wavelength. This enables to more easily generate a virtual phantom with the rendered artificial vital signs by using one or more projectors while maintaining the accuracy of the artificial vital signs.

In particular, the projected plurality of images each for a corresponding wavelength may be overlaid over each other. The overlaying may comprise an optical overlay, a spatial mixing (e.g. Bayer-pattern) or a temporal mixing (e.g. color-sequential). This allows the use of a light modulator, a micro-mirror device or a liquid crystal display (LCD) with a separate near-infrared (NIR) filter for a light source of the projector(s).

Preferably, the step of rendering is achieved by modulating a light signal to be emitted/absorbed from/by the provided virtual phantom, and/or by using a time sequential emission or absorption of a light signal to be emitted or reflected from the provided virtual phantom. The accuracy of the rendered vital signs is further improved. An Organic Light Emitting Diode (OLED) that provides a curved surface may be used to enable a 3D light-emitting phantom.

Preferably, the step of rendering comprises varying an absorption of a light signal by the provided virtual phantom. This may be achieved in combination with using a display for displaying the virtual phantom with the rendered artificial vital signs. In this way, the display is a passive display which does not emit light but rather locally varies its absorption of light. In particular, a surface of the display may be configured to modulate the absorption. If this surface is illuminated, the artificial vital sign can be measured from the varying reflected light. This resembles the skin more than a light-emitting phantom. The modulation of absorption may be achieved by using an LCD. In particular, the reflecting surface behind the LCD-modulator provides a reflective display. The surface can be further curved in order to resemble natural skin under real illumination conditions even more. The phantom may take the form of a doll. The display may be flat or curved.

Preferably, the step of rendering comprises emitting, reflecting, spatially and/or temporally varying an irradiation in one or more wavelength intervals from a range between 200 nm and 1200 nm.

Preferably, the rendered artificial vital sign comprises skin-tone variations over time reflecting the effects of pulse and respiratory signals as typically detectable with (remote) PPG-cameras on a natural person, i.e. with the detected relative amplitude being a function of wavelength.

Preferably, the output unit comprises a color monitor, a light modulator, a micro-mirror element, a projection display and/or a liquid crystal display (LCD) element. These examples of the output unit, e.g. display unit, enables to output or display the virtual phantom with the rendered artificial vital signs more reliably to the vital sign detector, e.g. vital sign camera, for the purpose of calibration or testing.

Preferably, the output unit is configured to operate in a non-visible, in particular near-infrared (NIR) spectral range and/or the LCD element comprises a NIR filter. This enables to mimic a natural body part showing natural vital sign(s) that can be detected in an environment with low illumination such as at night.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Vital signs such as blood volume pulse which induces a periodic change in the color of human skin can be detected using contact (PPG) sensors, and more recently using video cameras (rPPG). In this way, various vital signs (pulse, oxygenation level, respiration, etc.) can be monitored. Similarly, such sensors, in particular cameras, are utilized to monitor patient movements for sleep actigraphy and/or respiratory movement detection.

There is an increasing need to verify the calibration of these vital sign detectors e.g. vital sign cameras, once they have been introduced widely in hospitals. Also, prior to admitting new detectors to the market, the detectors may need to be tested for the sake of adequate performance.

To this end, the current invention proposes to use a virtual phantom, e.g. containing the form of a human body part (e.g. face) or a full-body, in an environment rendered at a monitor where the rendered skin mimics a natural body part/full-body showing one or more vital signs associated with the body part or full-body.

Such vital sign(s) may be "generated" on the virtual phantom, thereby leading to artificial vital signs rendered on the virtual phantom. For instance, for the case of the virtual phantom having the form of a human face, the artificial vital sign may comprise periodic variations of the skin color. Such a behavior of skin color can usually be observed on a natural human face due to pulse and/or respiration. Therefore, the rendered artificial vital signs enable to mimic a natural human face whose skin color changes periodically due to pulse and/or respiration.

The rendering of artificial vital signs involves the application of a mathematical model, in particular associated with parameters such as the shape, orientation, and color of the head, or full body. The parameters can be easily changed in order to mimic specific pulse-rates, respiratory signals and/or $SpO_2$ values that can be detected using vital signs cameras registering the virtual phantom. The virtual phantom, in particular together with the rendered artificial vital sign(s), may be provided by means of a software being run on a general purpose computer. Alternatively, the virtual phantom may be provided by means of a standalone device including the rendered artificial vital sign(s) to be registered by the vital signs camera under test.

Figure 1:
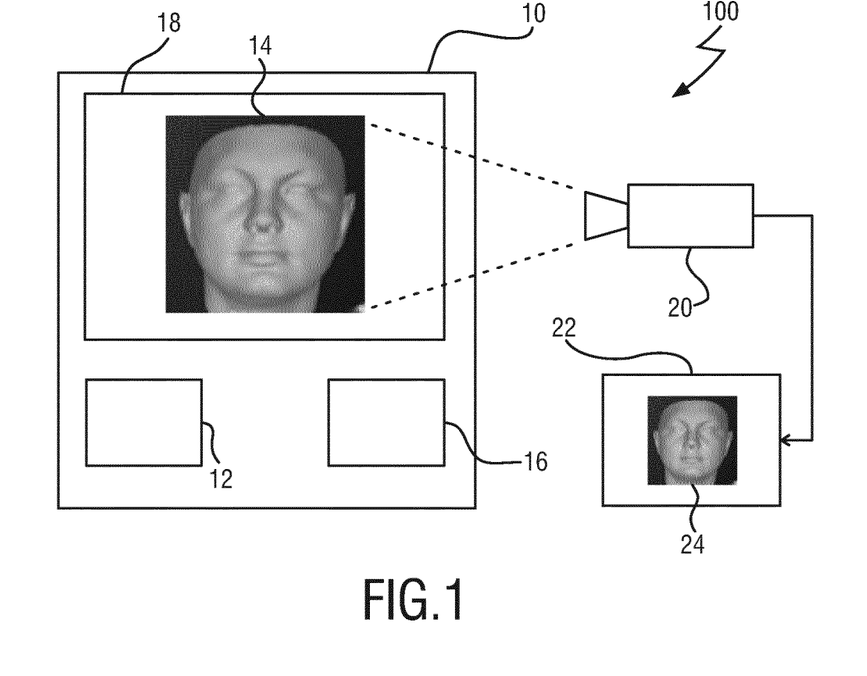
FIG. 1 shows a schematic block diagram of a first embodiment of a device according to the present invention.

FIG. 1 shows a schematic block diagram of a first embodiment of a device 10 for enabling to determine a setting of a vital sign detector 20. The device 10 comprises a virtual phantom providing unit 12 for providing a virtual phantom 14 of a living being. The living being may be a human and the virtual phantom 14 may accordingly have the form of a human face, as shown in FIG. 1.

Preferably, the human face is computed from a mathematical model run on the computer and exhibits temporal, in particular periodic variations in the skin color of the displayed face, e.g. one period or cycle per second. Such computed variations in the skin color mimic a periodic change caused by a pulse and/or a respiratory activity of a human being. Under illumination using visible light, the temporal variations in the skin color due to respiration and/or pulse are strongest in the green portion and weakest in red portion of the visible spectrum. This can be mimicked by displaying a computed human face which exhibits computed temporal variations in the skin color.

Further preferably, the display of the output unit 18 is capable of emitting or reflecting variable visible light, e.g. red (600-700 nm), green (500-600 nm) and blue (440-500 nm). Alternatively or additionally, the display of the output unit 18 is capable of emitting of reflecting variable NIR radiation of a plurality of different wavelength intervals, e.g. a first band around a center wavelength of 660 nm, a second band around a center wavelength of 800 nm and a third band around a center wavelength of 900 nm.

The virtual phantom providing unit 12 may comprise a communication interface or a wireless connection for transferring a prepared virtual phantom from an external entity, e.g. a storage medium or a communication network. The virtual phantom providing unit 12 may alternatively or additionally be configured to generate the virtual phantom 14 on its own, e.g. by means of computer simulation or by selecting from a plurality of optional virtual phantoms.

The device 10 further comprises a vital sign rendering unit 16 for rendering an artificial vital sign on the virtual phantom 14. The artificial vital sign may be rendered by using previously obtained results of vital sign measurements performed on a natural living being or natural tissues. Alternatively or additionally, the artificial vital sign may be, in contrast to natural vital signs of a natural living being or tissue, rendered using computer simulation involving a mathematical model. Preferably, the vital sign rendering unit 16 is configured to use a computer program to compute the artificial vital sign based on the mathematical model. In particular, artificial vital signs are added to the provided phantom using a mathematical model, or are based on a pre-recorded data-set that may have been recorded from a living being (e.g. human).

The device 10 further comprises an output unit 18 for outputting the virtual phantom 14 together with the rendered artificial vital sign to the vital sign detector 20. The output unit 18 is preferably, but not restricted to, a display unit for displaying the virtual phantom 14, in particular a monitor, e.g. an RGB color monitor. Alternatively, the output unit 18 may comprise a communication interface, a data interface and/or a storage unit. The virtual phantom 14 may comprise a synthetic video that can be displayed on an LCD monitor of the output unit 18.

Further preferably, the vital sign detector 20 may be a vital sign camera, e.g. an RGB camera, or a video health monitor. The vital sign detector 20 is connected to or contains itself a detector display unit 22, e.g. an RGB camera display, for displaying a detected vital sign signal. The detected vital sign signal comprises preferably a detected virtual phantom 24 received from the output unit 18 as shown in FIG. 1, further preferably together with one or more rendered artificial vital signs. In another embodiment, a contact sensor can be attached to the output unit 18, preferably the monitor, to be calibrated. In this case, the virtual phantom 14 may take the form of a piece of skin and/or a finger of a living being.

Based on the detected vital sign signal, a setting of the vital sign detector 20 can be determined. Preferably, the vital sign detector 20 can be calibrated or tested based on the received virtual phantom 24. For instance, the artificial vital sign rendered on the virtual phantom 14, 24 is preferably associated with a predetermined parameter such as a numeral value or a text description of a physiological state or category. Since the parameter is predetermined, the detected vital sign signal is associated with a known parameter, e.g. a known numeral value or a known physiological state or category. Based on the known parameter, the calibrated or tested vital sign detector 20 can be operated in order to detect a vital sign.

The temporal variations in the aforementioned example can be detected by the vital sign detector 20. In particular, the vital sign detector 20 may be configured to determine the vital sign as pulse and/or respiration with a predetermined pulse rate or respiratory rate by detecting a maximum in the color variation of the green portion of the visible spectrum while detecting a minimum in the color variation of the red portion of the visible spectrum.

The vital sign detector 20 may comprise a video health monitor operating in the near-infrared (NIR) spectrum range. In particular, the video health monitor may be operated under NIR illumination by the device 10, e.g. by a display of the output unit 18.

The display may comprise a projection display, onto which a plurality of images, each using light with a different wavelength, can be projected from one or more projectors, in order to provide the virtual phantom and/or to render the artificial vital sign. Preferably, the plurality of images are overlaid on top of each other in order to achieve optical superposition. This allows the use of an existing light-modulator, e.g. a micro-mirror device, or an LCD with a separate NIR-filter for the light-source used in each of the individual projectors. Further options for the display may include an array of light-emitters, and an array of light-modulators. Also a single modulated light-source (e.g. for a predetermined wavelength) can be used in combination with a scanning mechanism. (O)LED-arrays may be used that can operate in the NIR spectrum range.

The display of the output unit 18 may comprise a display using time-sequential emission of various wavelengths. In this case the, possibly time-varying, intensities per wavelength are multiplexed in time. The multiplexing of the intensities should be fast enough to guarantee that they are seen as simultaneously by the vital sign detector under test. This mode of operation is known from color sequential slide-projectors (beamers) that multiplex the red, green and blue color channels fast enough for them to be perceived by the human observer as being simultaneously available. Just like the human observer, the vital sign detection means typically have an integration time, which should be long compared to the cycle length of the color sequential multiplexing. Alternatively or additionally, the virtual phantom providing unit 12 may be configured to use time-sequential emission of various wavelengths.

The display of the output unit 18 may be a passive display, i.e. the virtual phantom and/or the artificial vital sign is not achieved based on light emitted from the display itself but rather based on locally varying the absorption level of light.

Preferably, the artificial vital sign such as pulse-rate and/or the respiratory rate may be rendered on the virtual phantom so that it varies over time. This can be achieved by simulating a temporally varying skin color of a human face using a mathematical model. For instance, the temporal or periodic variations of the skin color may be simulated to correspond to a pulse rate within a range, e.g. 30-240 beats per minute (bpm). In this way, irregular respiratory (apnea)

and pulse (arrhythmia) signals may be modeled. Further, the relative pulsatilities in different (e.g. NIR) wavelengths may be varied to mimic different $SpO_2$ values of a patient. For a subject with a near 100% arterial oxygenation, the pulsatility around 650 nm is very low compared to the relative pulsatility around other wavelengths (e.g. 800 nm). If the oxygenation level decreases in an unhealthy subject, the pulsatility around 650 nm increases relative to the strength at other wavelengths. The phantom could be configured to slowly cycle through the complete range of SpO2-values (e.g. 60% up to 100%) by varying the relative pulsatility in a band between 620 nm and 770 nm compared to the pulsatility at 800 nm (or another wavelength that has been selected). For any emulated SpO2-value the accuracy of the detector can consequently be established.

In yet other embodiments, instead of a face, a whole body of a patient is provided as the virtual phantom. Preferably, artificial vital signs comprising one or more motions are rendered on the patient body, e.g. motions that are typical for chest and/or abdominal breathing. Further preferably, such motions can be rendered as visualization of blanket movements due to motion of a person during sleep.

Further foreseen are embodiments where a person is rendered entering/leaving a bed to provide testing tools for camera-based bed-leave/entrance/falling detection. Again the rendering may be based on a mathematical model, or a visualization may be rendered from pre-recorded subjects performing the action under different conditions that could contain challenges for the detector under test.

Finally, the rendered person may exhibit movements typical for various sleep stages in order to test validate sleep-staging devices.

Figure 2:
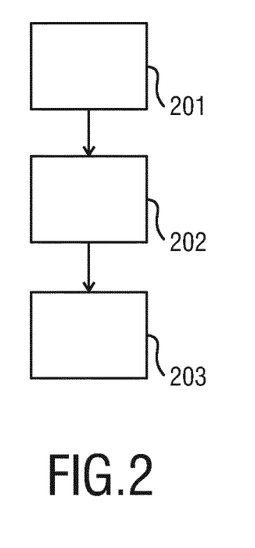
FIG. 2 shows a schematic block diagram of a method according to the present invention.

FIG. 2 shows a schematic block diagram of a method for enabling to analyze a property of a vital sign detector 20. The method comprises the steps 201-203. In step 201, a virtual phantom 14 of a living being is provided. In step 202, an artificial vital sign is rendered on the virtual phantom 14. In step 203, the virtual phantom 14 is output to the vital sign detector 20 together with the rendered artificial vital sign.

Figure 3:
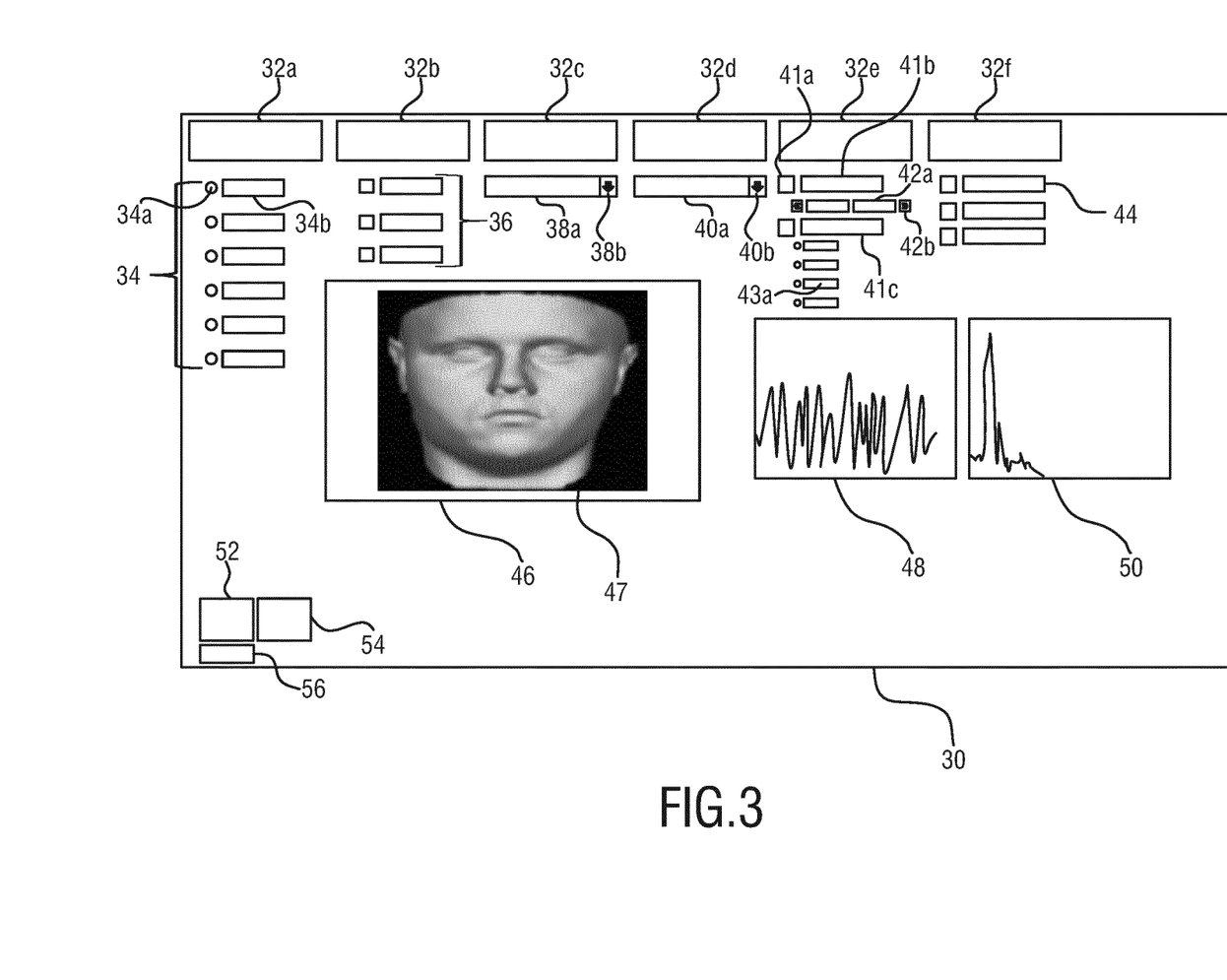
FIG. 3 shows illustratively an example of a user interface for configuring a virtual phantom and a plurality of artificial vital signs to be rendered on the virtual phantom.

FIG. 3 shows illustratively an example of a user interface 30 for configuring a virtual phantom and a plurality of artificial vital signs to be rendered on the virtual phantom.

The user interface 30 comprises a plurality of function buttons 32a-32f each for configuring an artificial vital sign. For instance, the function buttons 32a-32f may be used to configure the artificial vital signs "PPG Amplitude", "Pulse Rate" and "Motion", respectively. Further, function buttons for configuring phantom parameters, preferably "Ethnicity", "Illumination" and "Scene Background", may also be provided for configuring artificial vital signs related to the phantom parameters. Further examples for phantom parameters are strength and/or orientation of the light source and (possibly flickering) backgrounds that can be provided as additional challenges for the device under test, or to be calibrated. Preferably, the phantom parameter and/or artificial vital sign appear as a text string on the respective function button 32a-32f.

Under each of the function buttons 32a-32f, one or more selection fields are provided. For instance, under the function button 32a for configuring "Ethnicity", a number of selection bars 34b are listed (e.g. indicating skin-tones with different values on the Fitzpatrick scale) together with a selection activation circle 34a. After selecting the function button 32a which highlights the latter, the user can use a mouse or another pointing element to effect a selection among the selection bars 34b by clicking the corresponding selection activation circle 34a, which highlights the latter.

The selection bars 34b under "Ethnicity" may represent "Pale White", "White", "Cream White", "Moderate Brown", "Dark Brown" and "Dark", or any value in the range of Fitzpatrick's scale of skin-tones.

The highlighting may appear as filling the clicked selection activation circle 34a. Alternatively, as shown under the function button 32b for configuring "Illumination" in FIG. 3, a square may be used instead of a circle for selecting from the selection bars 36, which exemplarily could represent "Intensity", "Position (az, el)" and "Source Color (RGB)".

Another way of selection under a chosen function button 32a-32f is shown under the function button 32c for configuring "PPG Amplitude". A level bar 38a is provided for selecting a level being high, middle or low, which can be done by clicking on a downward arrow 38b adjacent to the level bar 38a. Similarly, the selection under the function button 32d "Pulse Rate" can be done by choosing a value for pulse rate shown in a level bar 40a by clicking a downward arrow 40b adjacent to the level bar 40a.

Under the function button 32e for configuring "Motion", the user can activate a first selection bar 41b representing "Motion Rate" by clicking a corresponding activation field 41a. The same can be done with a second selection bar 41c. A maximum bar 42a is subordinated to the first selection bar 41b for choosing a maximum motion rate by clicking a rightward arrow 42b. Analogously, a minimum motion rate can be chosen by clicking a leftward arrow, as shown in FIG. 3. A plurality of selection fields 43a representing different types of motions, preferably "Translation", "Rotation", "Scaling" and "Mixed", are subordinated to the second selection bar 41c.

The function button 32f for configuring "Scene Background" has a plurality of selection bars 44, preferably representing "Light Frequency", "Color (RGB)" and "Intensity". These selection bars 44 can be activated analogously to the selection bars 34b and 36.

By using the function buttons 32a-32f in combination with their corresponding subordinated selection fields, the user can configure a virtual phantom and render one or more artificial vital signs on the virtual phantom. In a display element 46, the configured virtual phantom 47 can be displayed, which takes the selected phantom parameter(s) and/or rendered artificial vital sign(s) into account.

A diagram display element 48, 50 may be provided to display a value of an artificial vital sign, preferably a temporal and/or periodic evolution or variation of the artificial vital sign. Such a temporal and/or periodic evolution or variation may be configured using one or more of the function buttons/selection fields provided on the user interface 30.

On the left lower corner of the user interface 30, an image selection field 52 may be provided for displaying the virtual phantom 47 as a static image, while a video selection field 54 is provided for displaying the virtual phantom 47 as a video clip. A clear button 56 may be available provided for clearing one or more selection previously made, and possibly return to a default setting.

The user interface 30 may be displayed on the output unit 18, the detector display unit 22 or another (external) entity. Further, the user interface 30 may be used to calibrate or test a camera-based, or contact-based motion-robust pulse-rate detector.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A method for enabling calibration of a vital sign camera, comprising the steps of:
   providing a virtual phantom of a living being, wherein the virtual phantom comprises a form of a face, a form of a full body, or a form of a body part, selected from a plurality of body part forms, corresponding to a body part during a specific stage of an illness or treatment;
   rendering one or more artificial vital signs on the virtual phantom, wherein the step of rendering comprises modulating a light signal to be emitted from the provided virtual phantom to simulate an external appearance of the one or more artificial vital signs as mimicking an appearance of one or more physical vital signs on the living being for calibration of the vital sign camera, wherein the one or more artificial vital signs are associated with a predetermined parameter relating to the one or more naturally occurring physical vital signs, and wherein the one or more artificial vital signs are based on one or more of a pre-recorded data set or a computer simulation;
   outputting the virtual phantom with the rendered one or more artificial vital signs to the vital sign camera; and
   determining a calibration setting of the vital sign camera based on detecting the predetermined parameter in one or more vital sign signals obtained by the vital sign camera by measuring the modulated light signal emitted from the virtual phantom.

2. The method according to claim 1, wherein at least one of the rendered one or more artificial vital signs is temporally varying.

3. The method according to claim 2, wherein the rendered one or more artificial vital signs comprise a periodic variation of a shape, a volume, a position, an orientation and/or a color of the provided virtual phantom.

4. The method according to claim 1, wherein the rendered one or more artificial vital signs are associated with a pulse activity, a respiratory activity, a concentration of a blood-component, a blood-pressure and/or a motion of the living being.

5. The method according to claim 1, wherein the step of rendering comprises projecting a plurality of images of the living being each for a corresponding wavelength.

6. The method according to claim 5, wherein the step of rendering further comprises overlaying the projected plurality of images over each other.

7. The method according to claim 1, wherein the step of rendering comprises using a time sequential emission or absorption of a light signal to be emitted or reflected from the provided virtual phantom.

8. The method according to claim 1, wherein the step of rendering comprises varying an absorption of a light signal by the provided virtual phantom.

9. The method according to claim 1, further comprising assigning a value to at least one of the rendered one or more artificial vital signs and/or identifying a motion associated with at least one of the rendered one or more artificial vital signs.

10. An apparatus to enable calibration of a vital sign camera, comprising:
    a processor; and
    non-transitory memory comprising instructions which, when executed by the processor, cause the apparatus to:
    provide a virtual phantom of a living being, wherein the virtual phantom comprises a form of a face, a form of a full body, or a form of a body part, selected from a plurality of body part forms, corresponding to a body part during a specific stage of an illness or treatment;
    render one or more artificial vital signs on the virtual phantom, wherein to render the one or more artificial vital signs comprises to modulate a light signal to be emitted from the provided virtual phantom to simulate an external appearance of the one or more artificial vital signs as mimicking an appearance of one or more physical vital signs on the living being for calibration of the vital sign camera, wherein the one or more artificial vital signs are associated with a predetermined parameter relating to the one or more physical vital signs, and wherein the one or more artificial vital signs are to be based on one or more of a pre-recorded data set or a computer simulation;
    output the virtual phantom with the rendered one or more artificial vital signs for detection of the predetermined parameter by the vital sign camera; and
    output, via a user interface, one or more values, including the predetermined parameter, associated with the rendered one or more artificial vital signs.

11. The apparatus according to claim 10, further comprising an output unit, the output unit comprising one or more of a color monitor, a light modulator, a micro-mirror element, a projection display and/or a liquid crystal display (LCD) element.

12. The apparatus according to claim 11, wherein the output unit is configured to operate in a near-infrared (NIR) spectral range and/or the LCD element comprises a NIR filter.

13. The apparatus according to claim 10, wherein at least one of the rendered one or more artificial vital signs is temporally varying, and wherein the rendered one or more artificial vital signs comprise a periodic variation of a shape, a volume, a position, an orientation and/or a color of the provided virtual phantom.

14. The apparatus according to claim 10, wherein the rendered one or more artificial vital signs are associated with a pulse activity, a respiratory activity, a concentration of a blood-component, a blood-pressure and/or a motion of the living being.

15. The apparatus according to claim 10, wherein to render the one or more artificial vital signs further comprises one or more of projecting a plurality of images of the living being each for a corresponding wavelength, using a time sequential emission or absorption of a light signal to be emitted or reflected from the provided virtual phantom, or varying an absorption of a light signal by the provided virtual phantom.

16. A non-transitory computer-readable storage medium comprising a set of instructions which, when executed by a computing system, cause the computing system to:
    provide a virtual phantom of a living being, wherein the virtual phantom comprises a form of a face, a form of a full body, or a form of a body part, selected from a plurality of body part forms, corresponding to a body part during a specific stage of an illness or treatment;

render one or more artificial vital signs on the virtual phantom, wherein to render the one or more artificial vital signs comprises to modulate a light signal to be emitted from the provided virtual phantom to simulate an external appearance of the one or more artificial vital signs as mimicking an appearance of one or more physical vital signs on the living being for calibration of a vital sign camera, wherein the one or more artificial vital signs are associated with a predetermined parameter relating to the one or more physical vital signs, and wherein the one or more artificial vital signs are to be based on one or more of a pre-recorded data set or a computer simulation;

output the virtual phantom with the rendered one or more artificial vital signs for detection of the predetermined parameter by the vital sign camera; and output, via a user interface, one or more values, including the predetermined parameter, associated with the rendered one or more artificial vital signs.

17. The non-transitory computer-readable storage medium according to claim 16, wherein at least one of the rendered one or more artificial vital signs is temporally varying.

18. The non-transitory computer-readable storage medium according to claim 17, wherein the rendered one or more artificial vital signs comprise a periodic variation of a shape, a volume, a position, an orientation and/or a color of the provided virtual phantom.

19. The non-transitory computer-readable storage medium according to claim 16, wherein the rendered one or more artificial vital signs are associated with a pulse activity, a respiratory activity, a concentration of a blood-component, a blood-pressure and/or a motion of the living being.

20. The non-transitory computer-readable storage medium according to claim 16, wherein to render the one or more artificial vital signs further comprises one or more of projecting a plurality of images of the living being each for a corresponding wavelength, using a time sequential emission or absorption of a light signal to be emitted or reflected from the provided virtual phantom, or varying an absorption of a light signal by the provided virtual phantom.

\* \* \* \* \*